(12) United States Patent
Kristen et al.

(10) Patent No.: US 6,756,505 B1
(45) Date of Patent: Jun. 29, 2004

(54) METALLOCENE COMPLEXES

(75) Inventors: Marc Oliver Kristen, Limburgerhof (DE); Holger Braunschweig, Aachen (DE); Carsten von Koblinski, Aachen (DE)

(73) Assignee: Basell Pololefine GmbH, Wesseling (DE)

( * ) Notice: Subject to any disclaimer, the term of this patent is extended or adjusted under 35 U.S.C. 154(b) by 0 days.

(21) Appl. No.: 09/868,101

(22) PCT Filed: Dec. 16, 1999

(86) PCT No.: PCT/EP99/10025

§ 371 (c)(1),
(2), (4) Date: Jun. 14, 2001

(87) PCT Pub. No.: WO00/35928

PCT Pub. Date: Jun. 22, 2000

(30) Foreign Application Priority Data

Dec. 16, 1998 (DE) .......................... 198 58 016

(51) Int. Cl.[7] .......................... C07F 17/00; B01J 31/00; C08F 4/44
(52) U.S. Cl. .............................. 556/7; 556/27; 556/53; 502/103; 502/117; 502/155; 526/132; 526/139; 526/161; 526/172; 526/943
(58) Field of Search ................................ 556/7, 27, 53; 502/103, 117, 155; 526/132, 139, 161, 172, 943

(56) References Cited

U.S. PATENT DOCUMENTS

| 5,679,812 A | 10/1997 | Winter | 556/7 |
|---|---|---|---|
| 5,962,718 A | 10/1999 | Reetz | 556/51 |
| 6,284,905 B1 * | 9/2001 | Ashe et al. | 556/7 |
| 6,376,406 B1 * | 4/2002 | Ashe et al. | 502/103 |
| 2001/0025115 A1 * | 9/2001 | Campbell et al. | 556/7 |

FOREIGN PATENT DOCUMENTS

| EP | 0 416 815 B1 * | 3/1991 |
|---|---|---|
| EP | 0 420 436 A1 * | 4/1991 |
| EP | 628 566 | 12/1994 |
| EP | 468 537 | 11/1996 |
| WO | WO 00/20426 | 4/2000 |

OTHER PUBLICATIONS

Jrl.Organ.Chem. 536–537(1997)361–373, Rufanov et al.
Orgometallics,1997,16,4546–4550,Stelcke et al.
Chem.Abst.,vol. 127, (No. 248187) (1997).
Chem.Abst.,vol. 132(No. 78649),(2000).
Jrl.Chem.Soc.1960,5168–5172Gerrard et al.
Chem.Com.(Cambridge,1991, 12, 1105–1106,Reetz et al.
Ing.Synth,1982,21, pp. 135–140,Manzer.
Chem.Abst.,vol. 131(No. 73736) (1999).
Chem.Abst.,vol. 130(No. 182572) (1999).
Angew.Chem.,1964, 76, p. 499.
Chemische Berichte 1956, 89 p. 434–443,Ziegler et al.
Jrl.Chem.Soc., 1960,3857–3861,Bradley et al.

* cited by examiner

*Primary Examiner*—Porfirio Nazario-Gonzalez
(74) *Attorney, Agent, or Firm*—Keil & Weinkauf

(57) ABSTRACT

In metallocene complexes of a metal of transition group IV, V or VI of the Periodic Table, at least one substituted or unsubstituted cyclopentadienyl radical is bound to an element of group III of the Periodic Table which is in turn a constituent of a bridge between this cyclopentadienyl radical and the metal atom and bears an organonitrogen, organophosphorus or organosulfur group as sole further substituent.

9 Claims, No Drawings

METALLOCENE COMPLEXES

The present invention relates to metallocene complexes of metals of transition group IV, V or VI of the Periodic Table, in which at least one substituted or unsubstituted cyclopentadienyl radical is bound to an element of group III of the Periodic Table which is in turn a constituent of a bridge between this cyclopentadienyl radical and the metal atom and bears an organonitrogen, organophosphorus or organosulfur group as sole further substituent.

Metallocene catalysts are gaining increasing importance in the polymerization of α-olefins. Metallocene catalysts are particularly advantageous for the copolymerization of ethylene with higher α-olefins since they result in particularly uniform incorporation of comonomer into the copolymer. Among metallocene catalysts, bridged metallocene complexes have attracted particular interest since they generally give a higher productivity than do the unbridged complexes, result in particularly good incorporation of comonomer and are also, for example, suitable for preparing highly isotactic polypropylene.

Bridge metallocene complexes in which the cyclopentadienyl radicals are joined by $SiMe_2$ or $C_2H_4$ bridges have been known for a long time. Such metallocene compounds are described, for example, in EP-A-336 128.

Apart from metallocene complexes in which the cyclopentadienyl radicals are bridged via silicon or carbon atoms, bridged metallocenes in which one or more boron atoms perform the bridging function are also known. Thus, for example, boron-bridged metallocene complexes in which the boron atom bears an alkyl or aryl substituent are known (J. Organomet. Chem., 1997, 536–537, 361). However, the preparation of these metallocene complexes is very complicated; nothing is known about polymerizations using these complexes.

DE-19 539 650 likewise describes bridged metallocene complexes in which boron, inter alia, may be present as bridge member. The boron atoms having a bridging function may be substituted by various radicals such as alkyl, aryl, benzyl and halogens and also by alkoxy or hydroxy groups. Once again, nothing is known about the polymerization behavior of such metallocene complexes.

Organometallics, 1997, 16, 4546, describes boron-bridged metallocenes in which the bridging boron atom is substituted by a vinyl group and is additionally coordinated by a Lewis base. However, the yields in the synthesis of these complexes are very poor and the polymerization of ethylene proceeds unsatisfactorily and leads only to low molecular weight polymer.

EP-A-0 628 566 describes bridged metallocene complexes whose generic formula nominates carbon, silicon, tin, germanium, aluminum, nitrogen, phosphorus and also boron as bridging atoms and in which the bridging atoms may be substituted by many substituents among which the dialkylamino group is mentioned. However, metallocene complexes having an amino-substituted boron bridge are not explicitly mentioned at any point, nor are properties of such complexes described.

The boron-bridged metallocene complexes known from the prior art are mostly difficult to prepare and do not offer, of offer only to a very restricted extent, the opportunity of influencing the electronic conditions in the cyclopentadienyl groups by means of electron-donating substituents on the boron atom and thus making it possible to influence the catalytic activity of the complexes.

It is an object of the present invention to provide metallocene complexes which no longer have the disadvantages described, are simple to prepare and, in particular, offer the opportunity of influencing the electronic conditions on the cyclopentadienyl radicals.

We have found that this object is achieved by the metallocene complexes mentioned at the outset. Furthermore, we have found a process for preparing such metallocene complexes and the use of the metallocene complexes as catalyst components for the homopolymerization and copolymerization of $C_2$–$C_{10}$-α-olefins.

As element of group III of the Periodic Table, particular mentioned may be made of boron and aluminum, with boron being particularly preferred.

Among the substituents which can act as the sole further substituent which occupies the third valence of the element of group III of the Periodic Table in addition to the bonds to a cyclopentadienyl radical and the other constituents of the bridge, particular mention may be made of organonitrogen, organophosphorus or organosulfur groups which, in addition to these heteroatoms, comprise up to 20 carbon atoms and up to 4 silicon atoms.

The metallocene complexes of the present invention may contain 1 or 2 cyclopentadienyl radicals. Preference is given to metallocene complexes of the formula I

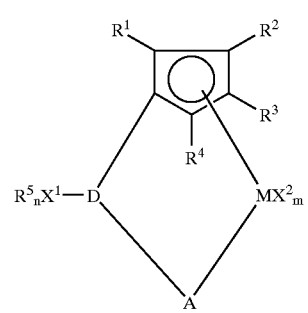

where the variables have the following meanings:

M is a metal atom of transition group IV, V or VI of the Periodic Table,

D is an element of group III of the Periodic Table, $R^1, R^2, R^3, R^4$ are each hydrogen, $C_1$- to $C_{10}$-alkyl, 5–7-membered cycloalkyl which may in turn bear a $C_1$–$C_{10}$-alkyl group as substituent, $C_6$- to $C_{15}$-aryl or arylalkyl, where two adjacent radicals $R^1$ to $R^4$ may also form 5–7-membered cyclic groups which may in turn bear $C_1$–$C_{10}$-alkyl groups or $SiR^6_3$ groups as substituents or include further fused-on ring systems, $R^5$ is hydrogen, $C_1$–$C_{10}$-alkyl, $C_6$–$C_{15}$-aryl or -arylalkyl or $C_1$–$C_{10}$-trialkylsilyl, $R^6$ is $C_1$–$C_4$-alkyl, m is the number of the transition group of the metal atom M minus 2, n is 2 when $X^1$ is nitrogen or phosphorus and is 1 when $X^1$ is sulfur, $X^1$ is nitrogen, phosphorus or sulfur, $X^2$ is hydrogen, $C_1$–$C_{10}$-hydrocarbyl, $N(C_1$–$C_{15}$-hydrocarbyl$)_2$ or halogen, A is a radical

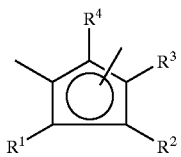

or a radical which is coordinated to M via an oxygen, sulfur, nitrogen or phosphorus atom.

Suitable metal atoms M are, in particular, the elements of transition group IV of the Periodic Table, i.e. titanium, zirconium and hafnium, with titanium and zirconium being preferred and zirconium being particularly preferred.

The cyclopentadienyl groups in formula I may be substituted or unsubstituted. Among the substituted metallocene complexes, those which are substituted by $C_1$–$C_4$-alkyl groups display particularly advantageous properties. Possible alkyl substituents are, for example, methyl, ethyl, n-propyl and n-butyl. The cyclopentadienyl radicals can be monosubstituted or polysubstituted, with monosubstituted and disubstituted cyclopentadienyl radicals having been found to be particularly advantageous. Preference is also given to cyclopentadienyl radicals in which 2 adjacent radicals $R^1$ to $R^4$ are joined to form 5- to 7-membered cyclic groups. Examples which may be mentioned are cyclopentadienyl groups derived from indenyl, tetrahydroindenyl, benzindenyl or fluorenyl, with these ring systems in turn being able to be substituted by $C_1$–$C_{10}$-alkyl groups or by trialkylsilyl groups.

In the metallocene complexes of the present invention having 2 cyclopentadienyl units, the bridging atom of the element of group III of the Periodic Table is directly bound to these two cyclopentadienyl units.

Among these dicyclopentadienyl complexes, particular preference is given to metallocene complexes in which A is a radical

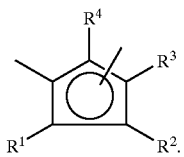

In the case of monocyclopentadienyl complexes, on the other hand, the radical A is not a cyclopentadienyl radical but rather a radical which is coordinated to M via an oxygen, sulfur, nitrogen or phosphorus atom. Possible groups A are, in particular, the following atoms or groups: —O—, —S—, —NR$^9$—, —PR$^9$— and uncharged 2-electron donor ligands such as —OR$^9$, —SR$^9$, —NR$^9{}_2$ or —PR$^9{}_2$. In these formulae, R$^9$ is hydrogen or an alkyl, aryl, silyl, halogenated alkyl or halogenated aryl group having up to 10 carbon atoms. Particular preference is given to metallocene complexes in which A is a group

—ZR$^7{}_2$—NR$^8$— in which

Z is silicon or carbon and

R$^7$,R$^8$ are hydrogen, silyl, alkyl, aryl or combinations of these radicals having up to 10 carbon or silicon atoms.

Examples of radicals R$^7$ and R$^8$ are, in particular, hydrogen, trimethylsilyl, methyl, tert-butyl and ethyl. Z is preferably a carbon atom.

In the metallocene complexes of the present invention, the bridging atom of the element of group III of the Periodic Table, which in itself has Lewis acid character, is substituted by a compound having Lewis base character. Due to its electron donor function, the Lewis base substituent influences the electronic conditions on the cyclopentadienyl radical and thus also the electronic environment of the metal atom. The Lewis base substituent can be bound to the bridging atom of the element of group III of the Periodic Table via a nitrogen, phosphorus or sulfur atom, with substituents having a nitrogen atom being particularly preferred. The atom $X^1$ can bear either hydrogen, $C_1$–$C_{10}$-alkyl groups or $C_1$–$C_{10}$-trialkylsilyl groups. Suitable alkyl groups are, in particular, $C_1$–$C_4$-alkyl groups and very particularly methyl or ethyl groups.

The central atom M is substituted not only by the ligands mentioned but also by ligands $X^2$. Suitable ligands $X^2$ are, in particular, lower alkyl groups such as methyl and ethyl, but $X^2$ is preferably halogen, particularly preferably chlorine.

The metallocene complexes of the present invention can be prepared in various ways. In the case of compounds having a bridging boron atom, for example, a method which has been found to be advantageous for preparing such metallocene complexes is to react a compound $R^5{}_nX^1$—$BY_2$ (II), where Y is halogen, with a compound

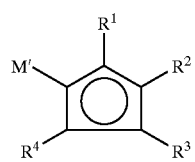

where M' is an alkali metal or alkaline earth metal, in the presence of a metal alkyl and then to allow the reaction product to react with an M halide compound and finally with an oxidant.

In formula (II), Y is preferably chlorine. The preparation of compounds of the formula (II) is described, for example, in Angew. Chem. 1964, 76, 499. The synthesis of the metallocene complexes of the present invention according to the above-described process is particularly simple and can be carried out in only one reaction vessel. The metal alkyl serves as deprotonating reagent; preference is given to using alkali metal alkyls or alkaline earth metal alkyls, in particular butyllithium. Suitable M halide compounds are, for example, titanium trichloride derivatives, particularly preferably titanium trichloride tris(THF) adduct. As oxidant in the final oxidation reaction, it is possible to use, for example, lead dichloride. After filtration of the reaction mixture, the metallocene complex can be isolated from the solution.

The metallocene complexes of the present invention can be used as catalyst components for the homopolymerization and copolymerization of $C_2$–$C_{10}$-α-olefins. To carry out the polymerization, it is generally necessary to convert the metallocene complexes into a cationic complex by means of suitable compounds capable of forming metalloceniuim ions. Possible compounds capable of forming metallocenium ions are, for example, aluminoxanes, preferably ones having a degree of oligomerization of from 3 to 40, particularly preferably from 5 to 30.

Apart from aluminoxanes, further cation-forming compounds are, in particular, borane and borate compounds which are a noncoordinating anion or can be converted into such an anion and form an ion pair with the metallocenium complex. Suitable reagents of this type for activating the metallocene complexes are well known to those skilled in the art and are described, for example, in EP-B1-0468537.

Particularly for polymerizations in the gas phase and in suspension, it may be necessary to apply the metallocene complexes and possibly the activating reagents to support materials. Such support materials and methods of applying catalyst complexes to supports are well known to those skilled in the art. Suitable support materials are, in particular, inorganic oxides such as silica gel, aluminum oxide or magnesium salts.

The above-described catalyst systems make it possible to prepare polyolefins, in particular polymers of 1-alkenes. For the purposes of the present invention, these are homopolymers and copolymers of $C_2$–$C_{10}$-alk-1-enes, with preferred monomers being ethylene, propylene, 1-butene, 1-pentene and 1-hexene. These catalyst systems are particularly useful for polymerizing ethylene with 1-butene or 1-hexene.

As polymerization processes, it is possible to employ all known processes, i.e., for example, gas-phase processes, suspension processes or polymerization processes in solution.

When used for the polymerization of ethylene and the copolymerization of ethylene with other α-olefins, the metallocene complexes of the present invention display good polymerization activity and lead to polymers having a relatively high molecular weight. The following examples illustrate the invention.

EXAMPLES

Syntheses of the ligands and complexes were carried out in the absence of air and moisture. The following reagents were prepared by literature methods: $(Me_3Si)_2NBCl_2$ (Angew. Chem. 1964, 76, 499), $Na(C_5H_5)$ (Chem. Ber. 1956, 89, 434), $Ti(NMe_2)_4$ (J. Chem. Soc., 1960, 3857), $[TiCl_3(THF)_3]$ (Inorg. Synth. 1982, 21, 135), $(C_4H_8N)_2BCl$ (Chem. Ber. 1994, 127, 1605), $(i-Pr)_2NBCl_2$ (J. Chem. Soc., 1960, 5168).

NMR: Varian Unity 500 at 499.843 MHz ($^1H$, internal standard: TMS), 150.364 MHz ($^{11}B$, $BF_3$*$OEt_2$ in $C_6D_6$ as external standard), 123.639 MHz ($^{13}C\{^1H\}$, APT, internal standard: TMS); unless indicated otherwise, all NMR spectra were recorded in $CD_2Cl_2$ as solvent. Mass spectra were recorded on a Finnigan MAT 95 (70 eV) and the elemental analyses (C, H, N) were obtained using a Carlo-Erba elemental analyzer, model 1106.

Example 1

Preparation of $Li_2[(Me_3Si)_2NB(C_5H_4)_2]$ (1)

8.23 g (93.54 mmol) of $Na(C_5H_5)$ were suspended in 100 ml of hexane. At room temperature, a solution of 11.13 g (46.05 mmol) of $(Me_3Si)_2NBCl_2$ in 20 ml of hexane was added dropwise. After stirring for 2 hours, the reaction mixture was cooled to 0° C. 57.6 ml (92.10 mmol) of a 1.6 molar solution of butyllithium in hexane were added dropwise. A white precipitate was formed immediately. The reaction mixture was warmed to room temperature and then stirred for another one hour. The volatile constituents were then removed under reduced pressure and the solid residue was extracted overnight using 150 ml of hexane. The mixture was filtered and the solid was dried under reduced pressure.

Yield: 14.13 g (98%) of white pyrophoric solid. $^1H$-NMR ($d_6$-THF): δ=0.01 (s, 18H, Si($CH_3$)$_3$), 5.83 (m, 4H, $C_5H_4$), 6.45 (m, 4H, $C_5H_4$). $^{11}B$-NMR: δ=46.6 (s); $^{13}C$-NMR: δ=4.31 (s, Si($CH_3$)$_3$), 103.16, 106.63, 116.63 ($C_5H_4$).

Example 2

Preparation of $Cl_2Ti[(C_5H_4)_2BN(SiMe_3)_2]$ (2)

Method A:

3.20 g (13.24 mmol) of $(Me_3Si)_2NBCl_2$ and 2.39 g (27.17 mmol) of $Na(C_5H_5)$ were reacted as described above. The resulting filtrate was admixed with 16.6 ml of a 1.6 molar solution of butyllithium in hexane. The slightly yellowish suspension was stirred at room temperature for 2 hours and then cooled to −100° C. 4.90 g (13.24 mmol) of $TiCl_3(THF)_3$ and 20 ml of THF were then added. The reaction mixture was warmed to room temperature, whereupon the color changed from light-brown to dark violet. The suspension was stirred for 3 hours and then treated with 1.84 g (6.62 mmol) of $PbCl_2$. After stirring for 16 hours, the volatile constituents were removed under reduced pressure. The solid obtained was extracted with 50 ml of dichloromethane and then filtered off. Yield: 4.43 g (80%) of dark red solid after the solution had been stored at −30° C.

$^1H$-NMR: δ=0.08 (s, 18H, Si($CH_3$)$_3$), 5.53 (m, 4H, $C_5H_4$), 7.05 (m, 4H, $C_5H_4$). $^{11}B$-NMR: δ=46.6 (s); $^{13}C$-NMR: δ=4.89 (s, Si($CH_3$)$_3$), 114.85, 133.44 ($C_5H_4$); MS: m/e (%): 417 (35) (M$^+$), 402 (15) (M$^+$-Me), 382 (25) (M$^+$—Cl); $C_{16}H_{26}NBCl_2Si_2Ti$ (418.18): calc.: C, 45.96, H, 6.27, N, 3.35; found: C, 46.56, H, 7.05, N, 2.87.

Example 3

Preparation of $(Me_2N)_2Ti[(C_5H_4)_2BN(SiMe_3)_2]$ (3)

2.08 g (8.60 mmol) of $(Me_3Si)_2NBCl_2$ and 1.51 g (17.20 mmol) of $Na(C_5H_5)$ were reacted as described above. The resulting filtrate was cooled to −30° C. and a solution of 1.93 g (8.60 mmol) of $Ti(NMe_2)_4$ in 5 ml of hexane was added dropwise. The reaction mixture was slowly warmed to room temperature, whereupon the color changed from yellow to dark red. After stirring for 1 hour, the volatile constituents were removed under reduced pressure and the resulting solid was suspended in 10 ml of hexane. After filtration and subsequent removal of the volatile constituents under reduced pressure, 1.05 g (28%) of (3) was obtained as a dark red solid.

$^1H$-NMR: δ=0.09 (s, 18H, Si($CH_3$)$_3$), 3.14 (s, 12H, N($CH_3$)$_2$), 5.42; (m, 4H, $C_5H_4$), 6.73 (m, 4H, $C_5H_4$). $^{11}B$-NMR: δ=46.9 (s); $^{13}C$-NMR: δ=4.89 (s, Si($CH_3$)$_3$), 51.11 (N($CH_3$)$_2$ 112.73, 131.66 ($C_5H_4$); $C_{20}H_{38}N_3BSi_2Ti$ (435.43): calc.: C, 55.17, H, 8.80, N, 9.65; found: C, 55.62, H, 8.22, N, 9.59.

Example 4

Peparation of $(Me_2N)ClTi[(C_5H_4)_2BN(SiMe_3)_2]$ (4)

1.09 g (4.50 mmol) of $(Me_2Si)_2NBCl_2$ and 0.88 g (10.00 mmol) of $Na(C_5H_5)$ were reacted as described above. The resulting filtrate was cooled to −30° C. and a solution of 1.01 g (4.50 mmol) of $Ti(NMe_2)_4$ in 5 ml of hexane was added dropwise. The reaction mixture was slowly warmed to room temperature. 0.84 g (4.50 mmol) of $(C_4H_8N)_2BCl$ was added to this solution. After stirring for 1 hour, the volatile constituents were removed under reduced pressure and the resulting solid was suspended in 20 ml of hexane. After filtration and subsequent storage at −30° C., 0.79 g (41%) of (4) was obtained as a dark red crystalline solid.

$^1H$-NMR ($CDCl_3$): δ=0.28 (s, 18H, Si($CH_3$)$_3$), 3.26 (s, 6H, N($CH_3$)$_2$), 5.08 (m, 2H, $C_5H_4$), 5.29 (m, 2H, $C_5H_4$), 6.62 (m, 2H, $C_5H_4$), 6.83 (m, 2H, $C_5H_4$). $^{11}B$-NMR: δ=46.4 (s); $^{13}C$-NMR: δ=7.53 (s, Si($CH_3$)$_3$), 57.54 (N($CH_3$)$_2$), 115.73, 117.57, 126.93, 128.54 ($C_5H_4$); $C_{18}H_{32}N_2BClSi_2Ti$ (426.80): calc.: C, 50.66, H, 7.56, N, 6.56; found: C, 50.23, H, 7.59, N, 6.39.

Example 5

Preparation of $Cl_2Ti[(C_5H_4)_2BN(SiMe_3)_2]$ (2)
Method B:

1.45 g (6.00 mmol) of $(Me_3Si)_2NBCl_2$ and 1.08 g (12.30 mmol) of $Na(C_5H_5)$ were reacted as described for (4). A solution of 1.34 g (6.00 mmol) of $Ti(NMe_2)_4$ in 5 ml of hexane was added dropwise to the filtrate obtained. The reaction mixture was subsequently admixed with 2.24 g (12.00 mmol) of $(C_4H_8N)_2BCl$. This gave 0.38 g (15%) of (2) as a dark red crystalline solid.

Example 6

Preparation of $(i\text{-}Pr)_2NB(C_5\text{—}H_5)_2$ (5)

A solution of 10.33 g (56.8 mmol) of $(i\text{-}Pr)_2NBCl_2$ in 25 ml of hexane was added dropwise at 20° C. to a suspension of 10.0 g (113.6 mmol) of $Na(C_5H_5)$ in 100 ml of hexane. After the exothermic reaction had abated, the mixture was stirred at 20° C. for 2 days. The $^{11}$B-NMR spectrum of the reaction solution then displayed only 1 signal at about 40 ppm for the disubstituted product (starting material: 31 ppm, mono-Cp-chloro product: 35 ppm). The reaction mixture was filtered to remove precipitated NaCl.

To prepare the pure compound, the solvent was removed under reduced pressure, leaving a yellowish orange, turbid oil. The residue was subjected to fractional distillation at $5*10^{-2}$ mbar. At the pressure indicated, the product was obtained at 72–75° C. initially as a clear, yellowish liquid, then after 10 minutes at 20° C. in the form of slightly yellowish, low-melting crystals (yield: 18%, thermolabile substance, substantial decomposition during distillation).

Analysis: $^{11}$B-NMR ($C_6D_6$): 40.18 ppm, $^1$H-NMR ($C_6D_6$): 1.06, 1.08, 1.14 (each doublet, $CH_3$ on isoprop., 3 isomers!); 2.85, 2.94, 3.04 (each multiplet, $CH_2$ on the Cp ring); 3.62–3.92 (3*multiplet, CH on isoprop.); 6.2–6.8 (multiplets, CH on the Cp ring). MS (EI) (fragment, %): 241 ($M^+$, 95%), 226 ($M'\text{-}CH_3$, 95%), 198 ($M^+$-iprop, 30%), 176 ($M^+$-Cp, 45%) (correct isotope pattern).

Example 7

Peparation of $(i\text{-}Pr)_2NB(C_5H_5)_2Li_2$ (6)

2 equivalents of butyllithium solution (1.6 M) were added dropwise at 10° C. to the filtrate of the reaction solution from (5), and the mixture was stirred overnight at 20° C., resulting in precipitation of a snow white solid. The solid was filtered off under protective gas and washed twice with 50 ml each time of hexane. This gave the dilithio salt as a white, highly pyrophoric powder in quantitative yield.

Analysis: $^1$H-NMR ($d_8$-THF): 1.23 ppm (doublet, $CH_3$); 4.52; (multiplet, CH on isoprop): 5.73 and 5.83 (each pseudo triplet, CH on Cp). $^{11}$B-NMR: $d_8$-THF: 41.86 ppm.

Example 8

Preparation of $(i\text{-}Pr)_2NB(C_5H_4)_2Ti(Cl)NMe_2$ (7)

A solution of 15 mmol of (5) in 30 ml of hexane was cooled to −60° C. and a solution of 3.35 g (15 mmol) of $Ti(NMe_2)_4$ in 10 ml of hexane was added dropwise. The solution was slowly warmed to 20° C., with the reaction solution taking on a distinct deep red color above about −15° C. The solution was stirred at 20° C. for 1 hour and reacted with 1.38 g (7.5 mmol) of $(C_4H_8N)_2BCl$, stirred at 20° C. for another 2 hours, evaporated to about 50% of its volume under reduced pressure and crystallized by storage at −30° C. After 1 day, the precipitated solid was filtered off. Yield: 3.02 g (55%) Analysis ($C_6D_6$): $^{11}$B-NMR: 40.3 ppm; $^1$H-NMR: 1.04 (d, 12H, $CHCH_3$); 3.10 (s, 6H, $N(CH_3)_2$; 4.87, 5.43, 6.70, 6.90 (each m, each 2H, $CH_{Cp}$); MS (EI): 366 ($M^+$, 15%), 322 ($M^+\text{-}NMe_2$, 100%), 287 ($M^+\text{-}NMe_2\text{-}Cl$, 10%), 176 ($TiCp_2$, 10%).

Example 9

Preparation of $(i\text{-}Pr)_2NB(C_5H_4)_2TiCl_2$ (8)

The preparation was carried out by a method analogous to the preparation of (7) using 5.9 mmol of (5) in 20 ml of hexane, 6.0 mmol (1.36 g) of $Ti(NMe_2)_4$ in 5 ml of hexane and 6.1 mmol (1.11 g) of $(C_4H_8N)_2BCl$.

Yield: 920 mg (43%); $^{11}$B-NMR: 40.7; $^1$H-NMR: 1.36 (d, 12H, $CHCH_3$); 5.61, 7.06 (each m, each 4H, $CH_{Cp}$).

Example 10

Preparation of $(Me_3Si)_2NB(C_5H_4)_2ZrCl_2$ (9)

4.13 g (11 mmol) of solid $ZrCl_4*2THF$ were added at −70° C. to a suspension of 3.7 g (11 mmol) of (1) in 30 ml of diethyl ether and rinsed in with 20 ml of toluene. The reaction mixture was slowly warmed to room temperature on the cooling bath, which resulted in the initially slightly yellowish color becoming more intense. The mixture was then stirred at room temperature for 16 hours. The solution was filtered and then evaporated to about 50% of its initial volume under reduced pressure. This solution was stored at −30° C. After 24 hours, yellow crystals were obtained. These were filtered off and the mother liquor was evaporated further and once again stored at −30° C. This gave yellow crystals. The combined yield was 3.92 g (86%).

$^1$H-NMR ($C_6D_6$): δ=0.11 (s, 18H, $SiMe_3$), 5.16, 6.62 (pseudo-t, 4H; CpH); $^{13}$C-NMR ($C_6D_6$): δ=5.0 (s, $SiMe_3$), 109.6, 124.9 (2s, CpH); $^{11}$B-NMR ($C_6D_6$): δ=47.4 (s); MS: m/e (%): 461 (5, $M^+$), 446 (3, $M^+$-Me), 91 (80, $Zr^+$), 66 (40, $Cp^+$).

Example 11

Preparation of $[iPr_2NB(C_5H_5)C_6H_5NH]$(10)

A solution of 5.4 g (30 mmol) of $iPr_2NBCl_2$ in 10 ml of hexane was added dropwise at 0° C. to a suspension of 2.64 g (30 mmol) of cyclopentadienylsodium in 25 ml of hexane. The mixture was allowed to come to room temperature and was stirred for another 2 hours. The precipitated NaCl was filtered off and the filtrate was slowly added dropwise at 0° C. to a suspension of 3.15 g (32 mmol) of lithium anilide in 20 ml of toluene. The mixture was allowed to warm to room temperature and was then stirred overnight to complete the reaction. The solvent was then removed under reduced pressure and the remaining yellow residue was taken up in 20 ml of benzene, filtered and the filtrate was freed of solvent. The solid obtained in this way was sublimed at 85° C. in a high vacuum. This gave 7.91 g of $iPr_2NB(C_5H_5)(C_6H_5NH)$ in virtually quantitative yield.

$^1$H-NMR(499.658 MHz, $CD_2Cl_2$): δ=1.23 (br. d, 12H, $CHCH_3$), 2.86 (m, 2H, $C_5H_5$), 3.59 (m, 2H, $CHCH_3$), 5.08 (br. s, 1H, NH), 6.2–7.2(m, 8H, $C_5H_5$, $C_6H_5$); $^{11}$B-NMR (160.310 MHz, $CD_2Cl_2$): δ=30,06. $^{13}$C-NMR(125.639 MHz, $CD_2Cl_2$): δ=23.96, 45.71, 43.44, 46.58 (br), 133.28 (Cp), 135.50 (Cp), 137.74 (Cp), 118.70, 119.64, 128.78, 146.10. MS(EI) [m/e,%]: 268 [$M^+$, 20], 253 [$M^+$-Me, 50], 93 [$C_6H_5NH_2^+$, 100], 65 [$C_5H_5^+$, 30]. Correct elemental analysis.

Example 12

Preparation of [iPr$_2$NB(C$_5$H$_5$)C$_6$H$_5$N{Ti(NMe$_2$)$_2$}] (11)

0.83 g (3.09 mmol) of (10) was dissolved in 15 ml of toluene and admixed at −78° C. with 0.69 g (3.09 mmol) of [Ti(NMe$_2$)$_4$] in 5 ml of toluene. After stirring at −78° C. for 20 minutes, the reaction mixture was allowed to warm slowly to room temperature and was stirred for another 2 hours at room temperature and another one hour at 40° C. The volatile constituents were removed under reduced pressure, the orange-red residue was taken up in 20 ml of hexane and the resulting solution was crystallized by cooling overnight at −30° C. This gave 0.97 g (78%) of the titanium complex (11) as an orange solid.

$^1$H-NMR(499.658 MHz, CD$_2$Cl$_2$): δ=0.90 (br., 6H, CHCH$_3$), 1.45 (br., 6H, CHCH$_3$), 2.97 (s, 12H, NMe$_2$), 3.31 (br., 2H, CHCH$_3$), 5.94 (m, 2H, C$_5$H$_4$), 6.44 (m, 2H, C$_5$H$_4$), 6.73 (m, 2H, C$_6$H$_5$), 6.83 (m, 1H, C$_6$H$_5$). $^{11}$B-NMR(160.310 MHz, CD$_2$Cl$_2$): δ=27.76; $^{13}$C-NMR(125.639 MHz, CD$_2$Cl$_2$): δ=21.36 (br), 27.01 (br), 44.62 (br), 46.11 (br), 47.90 (NMe$_2$) 120.95 (Cp), 124.00 (Cp), 115.81, 119.99, 128.16, 155.48. MS (EI) [m/e, %]: 402 [M$^+$, 45], 387 [M$^+$-Me, 5], 358 [M$^+$-NMe$_2$, 65], 314 [M$^+$-2 NMe$_2$, 1001, 93 [C$_6$H$_5$NH$_2^+$, 95], 64 [C$_5$H$_4^+$, 45]. Correct elemental analysis.

Example 13

Preparation of [iPr$_2$NB(C$_5$H$_4$)C$_6$H$_5$N{TiCl$_2$}](12)

0.50 g (4.60 mmol) of (CH$_3$)$_3$SiCl in 2 ml of hexane was added at 0° C. to a solution of 0.17 g (0.42 mmol) of the titanium complex (11) in 10 ml of hexane. The solution was warmed slowly to room temperature and stirred overnight. The yellow solid which precipitated was isolated by decanting off the supernatant solution and was washed twice with 10 ml each time of hexane. The solid obtained in this way was dried under reduced pressure. This gave 0.16 g of the titanium complex (12) in virtually quantitative yield.

$^1$H-NMR(499.658 MHz, CD$_2$Cl$_2$): δ=0.90 (d, 6H, J$^3$=6.71 Hz, CHCH$_3$), 1.54 (d, 6H, J$^3$=6.71 Hz, CHCH$_3$), 3.14 (m, 1H, J$^3$=6.71 Hz, CHCH$_3$), 3.41 (m, 1H, CHCH$_3$), 6.44 (m, 2H, C$_5$H$_4$), 7.08 (m, 2H, C$_5$H$_4$), 6.91 (m, 2H, C$_6$H$_5$), 7.14; (m, 1H, C$_6$H$_5$), 7.38 (m, 2H, C$_6$H$_5$). $^{11}$B-NMR(160.310 MHz, CD$_2$Cl$_2$): δ=28.39. $^{13}$C-NMR(125.639 MHz, CD$_2$Cl$_2$): δ=21.40, 27.72, 45.20, 47.28, 122.52 (Cp), 124.32, 127.21, 129.62, 152.39. MS(EI) [m/e, %]: 384 [M$^+$, 15], 369 [M$^+$-Me, 30], 348 [M$^+$-Cl, 50], 333 [M$^+$—C$_1$-2 Me, 20], 93(C$_6$H$_5$NH$_2^+$, 70], 64 [C$_5$H$_4$, 25]. Correct elemental analysis.

Example 14

Preparation of [iPr$_2$NB(C$_5$H$_5$)tBuNH](13)

A solution of 8.19 g (45 mmol) of iPr$_2$NBCl$_2$ in 30 ml of hexane was added dropwise at 0° C. to a suspension of 3.96 g (45 mmol) of cyclopentadienylsodium in 50 ml of hexane. The mixture was allowed to come to room temperature and was stirred for a further 16 hours. The precipitated NaCl was filtered off and the filtrate was slowly added dropwise at 0° C. to a suspension of 3.52 g (45 mmol) of LitBuNH in 20 ml of toluene. The reaction mixture was allowed to warm to room temperature and was then stirred overnight to complete the reaction. The solvent was then removed under reduced pressure and the remaining yellow residue was taken up in 50 ml of benzene, filtered and the filtrate was freed of the solvent. The solid obtained in this way was dried in a high vacuum. This gave 8.83 g of (iPr$_2$NB(C$_5$H$_5$)(tBuNH) (13) (79%).

$^1$H-NMR(499.658 MHz, C$_6$D$_6$): δ=1.08 (br. d, 6H, CHCH$_3$), 1.12; (br d, 6H, CHCH$_3$), 1.11 (s, 9H, C(CH$_3$)$_3$), 1.18 (S, 9H, C(CH$_3$)$_3$), 3.24 (m, 2H, CHCH$_3$), 3.37 (m, 2H, CHCH$_3$), 2.86 (m, 2H, CH$_{2Cp}$), 3.05 (m, 2H, CH$_{2Cp}$), 6.40–6.76 (m, 6H, C$_5$H$_4$). $^{11}$B-NMR (160.310 MHz, C$_6$D$_6$): δ=29.82. $^{13}$C-NMR(125.639 MHz, C$_6$D$_6$): δ=23.30, 33.31, 33.74, 33.96, 43.12, 46.9, 49.37, 49.64, 131.82, 133.82, 135.39. MS (EI) [m/e, %]: 248 [M$^+$,10], 233 [M$^+$-Me, 45]. Correct elemental analysis.

Example 15

Preparation of [iPr$_2$NB(C$_5$H$_4$)tBuN{Ti(NMe$_2$)$_2$}] (14)

0.71 g (2.87 mmol) of iPr$_2$NB(Cp)tBuNH (13) was dissolved in 10 ml of toluene and admixed at −78° C. with 0.64 g (2.87 mmol) of [Ti(NMe$_2$)$_4$] dissolved in 5 ml of toluene. After stirring at −78° C. for 20 minutes, the reaction mixture was allowed to warm slowly to room temperature and was stirred for another 2 hours at room temperature and another one hour at 40° C. The volatile constituents were removed under reduced pressure, the orange-red residue was taken up in 20 ml of hexane and the solution obtained in this way was crystallized by cooling overnight at −30° C. This gave 0.90 g (82%) of the titanium complex (14) as an orange solid.

$^1$H-NMR(499.658) MHz, C$_6$D$_6$): δ=1.17 (br d, 12H, CHCH$_3$), 3.19 (s, 12H, NMe$_2$), 3.62 (m, 2H, CHCH$_3$), 5.92(m, 2H, C$_5$H$_4$), 6.49 (m, 2H, C$_5$H$_4$), 6.73 (m, 2H, C$_6$H$_5$), 6.83 (m, 1H, C$_6$H$_5$), 7.14; (m, 2H, C$_6$H$_5$). $^{11}$B-NMR (160.310 MHz, C$_6$D$_6$): δ=29.82. MS(EI)[m/e,%]: 382 [M$^+$, 5], 339 [M$^+$—NMe$_2$,60], 248 [M$^+$-Ti-2NMe$_2$,35], 233 [M$^+$-Ti-2NMe$_2$-Me,100].

Example 16

Preparation of [iPr$_2$NB(C$_5$H$_4$)tBuN{TiCl$_2$}](15)

0.65 g (6 mmol) of (CH$_3$)$_3$SiCl in 2 ml of hexane was added at 0° C. to a solution of 0.45 g (1.18 mmol) of the titanium complex (14) in 10 ml of hexane. The solution was slowly warmed to room temperature and stirred for another 4 hours. The yellow solid which precipitated was isolated by decanting off the supernatant solution and was washed twice with 10 ml each time of hexane. The solid obtained in this way was dried under reduced pressure. This gave 0.38 g of the titanium complex (15) (88%).

$^1$H-NMR(499.658 MHz, C$_6$D$_6$): δ=0.85 (d, 6H, J$^3$=6.71 Hz, CHCH$_3$), 1.32 (d, 6H, J$^3$=6.71 Hz, CHCH$_3$), 3.04 (m, 1H, CHCH$_3$), 4.03; (m, 1H, CHCH$_3$), 6.22 (m, 2H, C$_5$H$_4$), 6.83 (m, 2H, C$_5$H$_4$). $^{11}$B-NMR(160.310 MHz, C$_6$D$_6$): δ=32.25. MS(EI)[m/e,%]: 365 [M$^+$, 5], 350 [M$^+$-Me,45], 322 [M$^+$-iPr,50].

Example 17

Ethylene polymerization:

General polymerization method:

In a 250 ml autoclave which had been flushed with inert gas, the amount indicated in Table 1 of the metallocene (with the central metal M=Ti or Zr) was dissolved in a little toluene. The appropriate amount of MAO (methylaluminoxane, 10% strength by weight in toluene) was then added thereto (Al:M=100:1). This gave a total volume of about 100 ml. The autoclave was then pressurized with ethylene to a pressure of 5 bar. The polymerization was carried out at 20° C. for 15 minutes. The autoclave was subsequently vented and the polymer was filtered off. Further data are given in Table 1.

TABLE 1

| Complex | Al:M (mol:mol) | Temp. (° C.) | Polym. time (min) | Amount used (mg/g) | Yield (g) | Activity (g of PE/g of cat. *h) | eta value (dl/g) |
|---|---|---|---|---|---|---|---|
| 7 | 100 | 20 | 15 | 18.6 | 24.4 | 5250 | 3.35 |
| 9 | 1000 | 20 | 15 | 24.4 | 17.04 | 3777 | n.d. |
| 9 | 650 | 60 | 5 | 10.2 | 7.74 | 9106 | n.d. |
| 12 | 1000 | 60 | 10 | 15.2 | 1.80 | 711 | 1.52 |
| 15 | 1000 | 60 | 30 | 13.2 | 0.98 | 148 | 0.93 | n.d.: not determined

We claim:

1. A metallocene complex of a metal of subgroup 5 or 6 of the Periodic Table of the Elements, in which at least one substituted or unsubstituted cyclopentadienyl radical is bonded to an element of group III of the Periodic Table of the Elements, which element of group III of the Periodic Table of the Elements is a constituent of a bridging member between this cyclopentadienyl radical and the metal atom, and which element of group III of the Periodic Table of the Elements carries, as the only other substituent, an organonitrogen, organophosphorus or organosulfur group.

2. A process for the preparation of a metallocene complex as of the formula

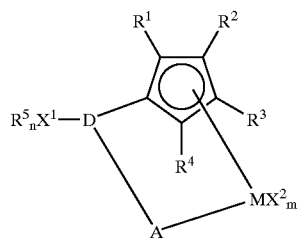

I in which

M is a metal atom of subgroup 4, 5 or 6 of the Periodic Table of Elements,

D is an element of group III of the Periodic Table of the Elements, $R^1$ $R^2$, $R^3$, $R^4$ are hydrogen $C_1$- to $C_{10}$-alkyl, 5–7 membered cycloalkyl, which can for its part be substituted by a $C_1$–$C_{10}$-alkyl group, or are $C_6$- to $C_{15}$-aryl or arylalkyl, where two neighboring radicals $R^1$ to $R^4$ can also form 5–7-membered cyclic groups, which for their part may be substituted by $C_1$–$C_{10}$-alkyl groups or $SiR^6_3$ groups, or may comprise further fused ring systems, $R^5$ is hydrogen, $C_1$–$C_{10}$-alkyl, $C_6$–$C_{15}$-aryl or -arylalkyl or $C_1$–$C_{10}$-trialkylsilyl, $R^6$ $C_1$–$C_4$-alkyl, m is the number of the subgroups of the metal atom M minus 2, n is 2 if $X^1$ is nitrogen or phosphorus, and is 1 if $X^1$ is sulfur, $X^1$ is nitrogen, phosphorus or sulfur, $X^2$ is hydrogen, $C_1$–$C_{10}$-hydrocarbyl, $N(C_1$–$C_{15}$-hydrocarbyl$)_2$ or halogen A is a radical

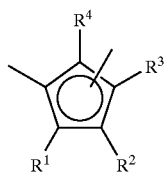

which comprises reacting a compound

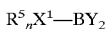  (II)

in which Y is halogen, with a compound (III)

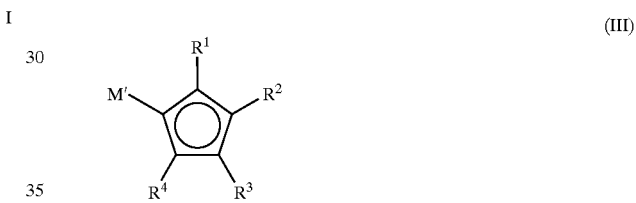

in which M' is an alkali metal or alkaline earth metal, in the presence of a metal alkyl, and then reacting the reaction product with an M halide compound and finally with an oxidizing agent.

3. A metallocene complex which is [iPr$_2$NB(C$_5$H$_5$)C$_6$H$_5$N{Ti(NMe$_2$)$_2$}] or [iPr$_2$NB(C$_5$H$_4$)C$_6$H$_5$N{TiCl$_2$}].

4. A metallocene complex which is Cl$_2$Ti[(C$_5$—H$_4$)$_2$BN(SiMe$_3$)$_2$], (Me$_2$N)$_2$Ti[C$_5$H$_4$)$_2$—BN(SiMe$_3$)$_2$], (Me$_2$N)ClTi[(C$_5$H$_4$)$_2$BN(SiMe$_3$)$_2$], (i-Pr)$_2$NB(C$_5$H$_4$)$_2$Ti(Cl)NMe$_2$ or (Me$_3$Si)$_2$NB(C$_5$H$_4$)$_2$ZrCl$_2$.

5. A process for the homo- or copolymerization of $C_2$–$C_{10}$-α-olefins which comprises (co)polymerizing the $C_2$–$C_{10}$-α-olefins in the presence of the metallocene complex defined in claim 1.

6. A metallocene complex of the formula I

I

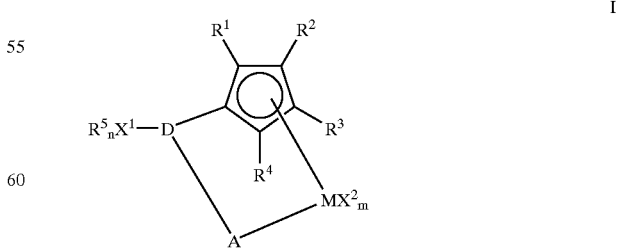

in which

M is a metal atom of subgroup 4, 5 or 6 of the Periodic Table of Elements,

D is an element of group III of the Periodic Table of the Elements, $R^1$, $R^2$, $R^3$, $R^4$ are hydrogen, $C_1$- to $C_{10}$-alkyl, 5–7-membered cycloalkyl, which can for its part be substituted by a $C_1$–$C_{10}$-alkyl group, or are $C_1$- to $C_{15}$-aryl or arylalkyl, where two neighboring radicals $R^1$ to $R^4$ can also form 5–7-membered cyclic groups, which for their part may be substituted by $C_1$–$C_{10}$-alkyl groups or $SiR^6{}_3$ groups, or may comprise further fused ring systems, $R^5$ is hydrogen, $C_1$–$C_{10}$-alkyl, $C_6$–$C_{15}$-aryl or -arylalkyl or $C_1$–$C_{10}$-trialkylsilyl, $R^6$ $C_1$- to $C_4$-alkyl, m is the number of the subgroups of the metal atom M minus 2, n is 2 if $X^1$ is nitrogen or phosphorus, and is 1 if $X^1$ is sulfur, $X^1$ is nitrogen, phosphorus or sulfur, $X^2$ is hydrogen, $C_1$–$C_{10}$-hydrocarbyl, $N(C_1$–$C_{15}$-hydrocarbyl$)_2$ or halogen A is —O—, —S—, —$OR^9$, or —$SR^9$, wherein $R^9$ is hydrogen or alkyl, aryl, silyl, halogenated alkyl or halogenated aryl comprising up to 10 carbon atoms.

7. A metallocene complex of a metal of subgroup 4, 5 or 6 of the Periodic Table of the Elements, in which at least one substituted or unsubstituted cyclopentadienyl radical is bonded to an element of group III of the Periodic Table of the Elements, which element of group III of the Periodic Table of the Elements is a constituent of a bridging member between this cyclopentadienyl radical and the metal atom, and which element of group III of the Perodic Table of the Elements carries, as the only other substituent, an organophosphorous, or organosulfur group.

8. A process for the homo- or copolymerization of α-olefins which comprises (co)polymerizing $C_2$–$C_{10}$-α-olefins in the presence of the metallocene complex of claim 6.

9. A process for the homo- or copolymerization of α-olefins which comprises (co)polymerizing $C_2$–$C_{10}$-α-olefins in the presence of the metallocene complex of claim 7.

* * * * *

UNITED STATES PATENT AND TRADEMARK OFFICE
CERTIFICATE OF CORRECTION

PATENT NO.   : 6,756,505 B1
DATED        : June 29, 2004
INVENTOR(S)  : Kristen et al.

It is certified that error appears in the above-identified patent and that said Letters Patent is hereby corrected as shown below:

Column 11,
Line 15, "subgroup 5 or 6" should read -- subgroup 4, 5 or 6 --.

Signed and Sealed this

Twenty-second Day of March, 2005

JON W. DUDAS
*Director of the United States Patent and Trademark Office*